United States Patent
Bathe et al.

(10) Patent No.: US 6,703,509 B2
(45) Date of Patent: Mar. 9, 2004

(54) METHOD FOR PRODUCING 5-ARYL NICOTINALDEHYDES

(75) Inventors: Andreas Bathe, Darmstadt (DE); Heinz Bokel, Darmstadt (DE); Thomas Keil, Fischbachtal (DE); Ralf Knieriemen, Gross-Zimmern (DE); Christoph Murmann, Reinheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/203,159

(22) PCT Filed: Jan. 5, 2001

(86) PCT No.: PCT/EP01/00083

§ 371 (c)(1),
(2), (4) Date: Aug. 6, 2002

(87) PCT Pub. No.: WO01/58873

PCT Pub. Date: Aug. 16, 2001

(65) Prior Publication Data

US 2003/0055259 A1 Mar. 20, 2003

(30) Foreign Application Priority Data

Feb. 7, 2000 (DE) .......................................... 100 05 150

(51) Int. Cl.$^7$ .................... C07D 211/78; C07D 213/46; C07D 211/70
(52) U.S. Cl. ...................... 546/315; 546/318; 546/319; 546/339; 546/341
(58) Field of Search ............................... 546/315, 318, 546/319, 339, 341

(56) References Cited

U.S. PATENT DOCUMENTS 5,585,388 A 12/1996 Cosford et al.

FOREIGN PATENT DOCUMENTS

| EP | 0 905 458 | * | 4/1999 |
| EP | 0 908 458 A1 | | 4/1999 |
| WO | WO 9705131 | * | 2/1997 |
| WO | WO 9732873 | * | 9/1997 |
| WO | WO 9920617 | * | 4/1999 |
| WO | WO 9942446 | * | 8/1999 |

OTHER PUBLICATIONS

Julia, CA 65:99237, abstract of Bull Soc Chim France, 1966, (7), 2387–2394.*
S. Marquais et al., "Aryl–Aryl Cross Coupling On A Solid Support Using Zinc Organic Reagents and Palladium Catalysis," Tetrahedron Letters, NL, Elsevier Science Publishers, Amsterdam, Bd. 37, Nr. 31, Jul. 29, 1996, pp. 5491–5494, XP004029432, Issn: 0040–4039.
K. Nagayama et al., "Direct Hydrogenation of Carboxylic Acids To Corresponding Aldehydes Catalyzed by Palladium Complexes In The Presence of Pivalic Anhydride," Chemistry Letters, Nr. 11, 1988, pp. 1143–1144, XP000999904, Chemical Society of Japan, Tokyo, JP, ISSN: 0366–7022.
W.J. Thomson et al.," An Efficient Synthesis of Arylpyrazines In Bipyridines," Journal of Organic Chemistry, US, Americam Chemical Society, Easton, Bd. 53, 1988, pp. 2052–2055, XP002143541, ISSN: 0022–3263.
G. Lapuyade et al., "Derives Alkyles et Aryles De L'Acide Nipecotique: Synthese et Appreciation De L'Activite Inhibitrice De La Capure Du Gaba En Fonction De Parametres Conformationnels et de Biodisponibilite. Alkyl and Aryl Derivatives of Nipecotic Acid: Synthesis and Inhibition of Gaba Uptake as A Function of Conform," European Journal of Medicinal Chemistry, Chimica Therapeutica, Fr. Editions Scientifique Elsevier, Paris, Bd. 22, Nr. 5, Sep. 1, 1987, pp. 383–391, XP002035295, ISSN: 0223–5234.
W.J. Thomson et al., Journal of Organic Chemistry., Bd. 49, Nr. 26, 1984, pp. 5237–6243, XP000999537, American Chemical Society, Easton, US, ISSN: 0022–3263.

* cited by examiner

Primary Examiner—D. Margaret Seaman
(74) Attorney, Agent, or Firm—Millen, White, Zelano & Branigan, P.C.

(57) ABSTRACT

The invention relates to a process for the preparation of 5-arylnicotinaldehydes by reduction of the corresponding 5-arylnicotinic acids by catalytic hydrogenation in the presence of carboxylic anhydrides in which the catalyst used is a palladium/ligand complex, characterized in that the molar ratio between palladium and ligand is from 1:5 to 1:15 in the case of monodentate ligands and from 1:2.5 to 1:7.5 in the case of bidentate ligands.

8 Claims, No Drawings

METHOD FOR PRODUCING 5-ARYL NICOTINALDEHYDES

The invention relates to a process for the preparation of 5-arylnicotinaldehydes by reduction of the corresponding 5-arylnicotinic acids by catalytic hydrogenation in the presence of carboxylic anhydrides in which the catalyst used is a palladium/ligand complex, characterized in that the molar ratio between palladium and ligand is from 1:5 to 1:15 in the case of monodentate ligands and from 1:2.5 to 1:7.5 in the case of bidentate ligands.

5-Arylnicotinaldehydes are important intermediates and end products in industrial organic chemistry. Appropriately substituted derivatives are, in particular, valuable intermediates in the synthesis of highly value-added end products or are themselves such end products, in particular for crop protection, such as, for example, fungicides, insecticides, herbicides or pesticides, or for the preparation of substances having high pharmaceutical activity. Production of the corresponding 5-arylnicotinaldehydes on an industrial scale makes highly economical and environmentally friendly preparation necessary.

The 5-arylnicotinaldehydes are distinguished by an unexpected sensitivity to oxidation and disproportionation. Consequently, the methods described in the literature for the preparation of these compounds by chemoselective reduction of aromatic acids or their esters or by oxidation of aromatic alcohols cannot be applied to a satisfactory extent to the corresponding 5-arylnicotinic acid or the corresponding 5-arylnicotinyl alcohol.

Methods for the reduction of nicotinic acid are known. Thus, for example, the reduction of nicotinic acid by palladium-catalysed hydrogenation is described in Chemistry Letters 1998, 1143–1144. The process disclosed therein is carried out in the presence of pivalic anhydride (trimethylacetic anhydride), giving, in the case of unsubstituted nicotinic acid, the corresponding aldehyde in good yields.

However, if substituted nicotinic acids and in particular aromatic-substituted nicotinic acids are employed in this process, considerable losses of yield occur. In addition, the use of pivalic acid is associated with considerable costs, and consequently this process is not suitable for industrial application.

The object on which the invention is based was to discover a process for the preparation of 5-arylnicotinaldehydes which makes inexpensive and environmentally friendly access even to this class of substances possible without the above-mentioned disadvantages.

Surprisingly, it has now been found that 5-arylnicotinaldehydes can be obtained by reduction of the corresponding 5-arylnicotinic acids by catalytic hydrogenation in the presence of carboxylic anhydrides in which the catalyst used is a palladium/ligand complex if a molar ratio between palladium and ligand of from 1:5 to 1:15 is observed in the case of monodentate ligands and of from 1:2.5 to 1:7.5 in the case of bidentate ligands.

The measure according to the invention also allows the use of other carboxylic anhydrides which are less expensive than pivalic anhydride and which, without an excess of ligand, give only a low yield of product.

The invention thus relates to a process for the preparation of 5-arylnicotinaldehydes by reduction of the corresponding 5-arylnicotinic acids by catalytic hydrogenation in the presence of carboxylic anhydrides in which the catalyst used is a palladium/ligand complex, characterized in that the molar ratio between palladium and ligand is from 1:5 to 1:15 in the case of monodentate ligands and from 1:2.5 to 1:7.5 in the case of bidentate ligands.

The invention preferably relates, in particular, to a process for the preparation of 5-arylnicotinaldehydes of the formula I

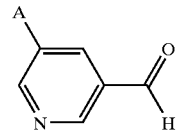

in which
A is a phenyl radical or naphthyl radical, each of which is unsubstituted or monosubstituted or polysubstituted by R, F, Cl, Br, I, —CN, —NO$_2$, —CF$_3$, —OCF$_3$, —OCHF$_2$, —OCF$_2$CF$_3$, —OCHFCF$_3$ or —OH and in which, in addition, one or more CH groups may be replaced by N, and
R is H, a straight-chain or branched alkyl radical having 1 to 15 carbon atoms which is monosubstituted by —CF$_3$ or at least monosubstituted by fluorine, where, in addition, one or more CH$_2$ groups in these radicals may each, independently of one another, be replaced by —S—, —O—, —O—CO—, —CO—O— or —CH=CH— in such a way that heteroatoms are not directly adjacent,
by reduction of the corresponding 5-arylnicotinic acids by catalytic hydrogenation in the presence of carboxylic anhydrides in which the catalyst used is a palladium/ligand complex, characterized in that the molar ratio between palladium and ligand is from 1:5 to 1:15 in the case of monodentate ligands and from 1:2.5 to 1:7.5 in the case of bidentate ligands.

The invention furthermore relates to the use of the 5-arylnicotinaldehydes for the preparation of N-alkylated amines by reaction of the 5-arylnicotinaldehydes with primary amines to give the corresponding imines, followed by reduction. The reaction of the aldehydes with the amines and also the reduction of the imines can be carried out by methods known per se, as described in the literature (for example in standard works, such as Houben-Weyl, Methoden der organischen Chemie [Methods of Organic Chemistry], Georg-Thieme-Verlag, Stuttgart, or Organikum [Organic Chemistry], 17$^{th}$ Edition, VEB Deutscher Verlag der Wissenschaften, Berlin, 1988), to be precise under reaction conditions which are known and are suitable for the said reactions.

The compounds of the formula I are, in particular, highly suitable for the preparation of N-alkylated amines of the formula X:

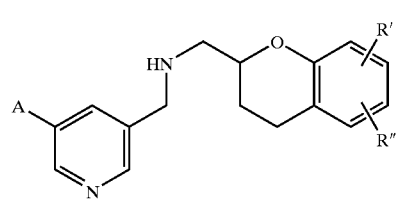

In which
R' and R", independently of one another, are as defined for R or are F, Cl, Br, I, —CN, —NO$_2$, —CF$_3$, —OCF$_3$, —OCHF$_2$, —OCF$_2$CF$_3$, —OCHFCF$_3$ or —OH, and A is as defined above, by reaction of the corresponding amines and reduction of the resultant imines by conventional reduction processes, in particular by catalytic hydrogenation or by using borohydrides, such as, for example, sodium borohydride.

Similar compounds are already known from EP 0707007.

Preference is given to the use of the aldehyde of the formula I in which A is 4-fluorophenyl for the preparation of (R)-2-[5-(4-fluorophenyl)-3-pyridylmethylaminomethyl] chroman by reaction with R-chromanamine and reduction of the resultant imine.

In the preferred compounds of the formulae above and below, R is H, an alkyl or alkoxy group having 1 to 10 carbon atoms or an alkenyl group having 2 to 7 carbon atoms.

A is preferably a phenyl group, a phenyl group which is monosubstituted or disubstituted by F, a 4-fluorophenyl group, a pyrimidyl, a pyridyl, a pyrazyl or a pyridazyl group, in particular a 4-fluorophenyl group.

Preference is given to compounds which contain at least one of the preferred radicals.

If R is an alkyl group, in which, in addition, one $CH_2$ group (alkoxy or oxaalkyl) may be replaced by an O atom, it may be straight-chain or branched. It preferably has 2, 3, 4, 5, 6, 7, 8, 9 or 12 carbon atoms and accordingly is preferably ethyl, propyl, butyl, pentyl, hexyl, heptyl, octyl, nonyl, decyl, ethoxy, propoxy, butoxy, pentoxy, hexyloxy, heptyloxy, octyloxy, nonyloxy or decyloxy, furthermore also undecyl, dodecyl, undecyloxy, dodecyloxy, 2-oxapropyl (=2-methoxymethyl), 2-oxabutyl (=methoxyethyl) or 3-oxabutyl (=2-ethoxymethyl), 2-, 3- or 4-oxapentyl, 2-, 3-, 4- or 5-oxahexyl, or 2-, 3-, 4-, 5- or 6-oxaheptyl. Particular preference is given to hexyl, pentyl, butyl, n-butyl, propyl, i-propyl, methyl and ethyl, in particular propyl and pentyl; particularly preferred alkoxy groups are hexyloxy, pentoxy, n-butoxy, propoxy, i-propoxy, methoxy and ethoxy, in particular ethoxy and n-butoxy. Compounds of the formulae above and below which have branched wing groups R may be of importance. Branched groups of this type generally contain not more than two chain branches. R is preferably a straight-chain group or a branched group having not more than one chain branch.

Preferred branched radicals are isopropyl, 2-butyl (=1-methylpropyl), isobutyl (=3-methylpropyl), tert-butyl, 2-methylbutyl, isopentyl (=3-methylbutyl), 2-methylpentyl, 3-methylpentyl, 4-methylpentyl, 2-ethylhexyl, 5-methylhexyl, 2-propylpentyl, 6-methylheptyl, 7-methyloctyl, isopropoxy, 2-methylpropoxy, 2-methylbutoxy, 3-methylbutoxy, 2-methylpentoxy, 3-methylpentoxy, 2-ethylhexyloxy, 1-methylhexyloxy, 1-methylheptyloxy, 2-oxa-3-methylbutyl and 3-oxa-4-methylpentyl.

The radical R may also be an optically active organic radical containing one or more asymmetrical carbon atoms.

The process according to the invention is very particularly suitable for the preparation of the aldehydes of the formulae I1 to I10:

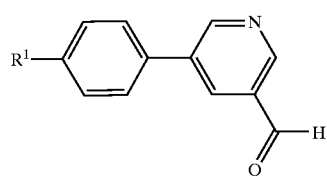

I1

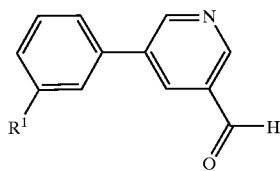

I2

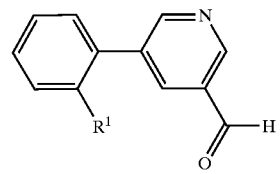

I3

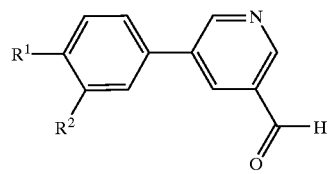

I4

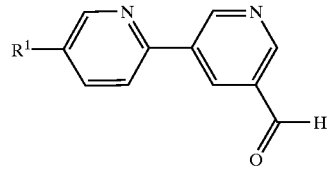

I5

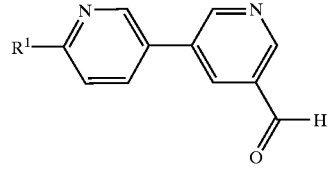

I6

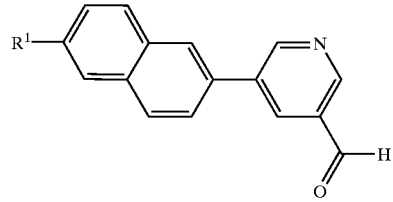

I7

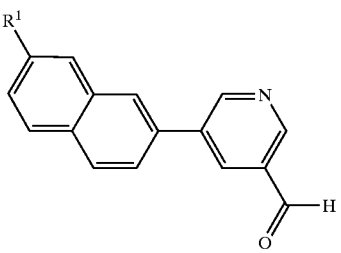

I8

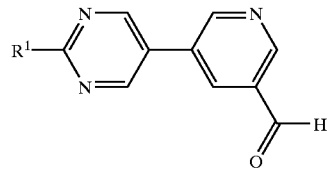

I9

-continued

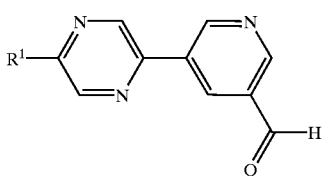

I10

In which $R^1$ and $R^2$ independently of one another, are as defined for R and are in particular F, —$CF_3$, —$OCF_3$, —$OCHF_2$ or H, and are very particularly preferably F.

Very particularly preferred 5-arylnicotinaldehydes which can be prepared by the process according to the invention are the compounds of the formulae I1, I2, I9 and I10.

The 5-arylnicotinic acids used as starting materials for the process according to the invention are either known or are prepared by methods known per se, as described in the literature (for example in standard works, such as Houben-Weyl, Methoden der organischen Chemie [Methods of Organic Chemistry], Georg-Thieme-Verlag, Stuttgart), to be precise under reaction conditions which are known and suitable for said reactions. However, use can also be made of variants which are known per se, but are not mentioned here in greater detail.

The 5-arylnicotinic acids are preferably prepared by Suzuki coupling (N. Miyaura, A. Suzuki, Chem. Rev. 95, 2457 (1995)) by reacting 5-bromonictonic acid, an alkyl 5-bromonicotinate, 5-bromonicotinyl alcohol or the alkylcarboxylic acid ester thereof with the corresponding arylboronic acids under known reaction conditions to give a compound of the formula II, III, IV or V:

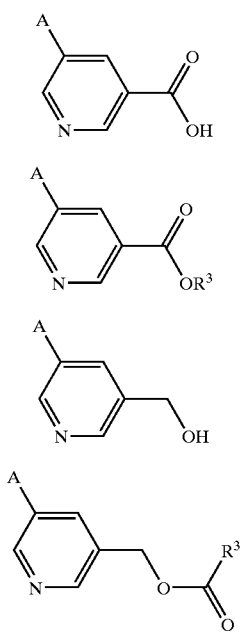

In which A is as defined above, and $R^3$ is methyl, ethyl, n-propyl, isopropyl, n-butyl, sec-butyl or tert-butyl, subsequently hydrolysing the ester of the formulae III or V by conventional processes to give the free acid of the formula II or the alcohol of the formula IV, and oxidizing the alcohol of the formula IV by conventional methods to give the acid of the formula II.

The acids of the formula II obtained in this way can be used directly for the process according to the invention.

$R^3$ is preferably methyl or ethyl, in particular methyl.

Compounds of the formulae I, II, III and IV in which A is a 4-fluorophenyl radical are particularly preferred.

The invention likewise relates to the novel compounds of the formulae I, II, III and IV.

The reaction in the process according to the invention for the preparation of 5-arylnicotinaldehydes is simple to carry out, with the 5-arylnicotinic acids in question preferably being hydrogenated in organic solvents, at temperatures of from 10 to 180° C., preferably at from 20 to 150° C. and very particularly preferably from at 40 to 100° C., and at a pressure of from 1 to 150 bar, preferably at from 1.5 to 120 bar and in particular at from 2 to 100 bar, with addition of a carboxylic anhydride in the presence of a palladium/ligand complex.

The solvents used for the process according to the invention are preferably ethers, such as, for example, diethyl ether or tetrahydrofuran, ketones, such as, for example, acetone, hydrocarbons, such as, for example, toluene, benzene, hexane or heptane, amides, such as, for example, dimethylformamide or N-methylpyrrolidone, or acid anhydrides, such as, for example, acetic anhydride.

Particular preference is given to ethers, in particular tetrahydrofuran.

Mixtures of the said solvents can likewise be used.

The amount of solvent is not crucial; from 10 g to 500 g of solvent can preferably be added per g of the compound of the formula II to be reacted.

The duration of the reaction depends on the selected reaction conditions. In general, the reaction duration is from 0.5 hour to 10 days, preferably from 1 to 24 hours.

In a preferred embodiment of the invention, the end of the reduction to the aldehyde is determined by suitable analytical methods, for example HPLC, and the reduction is interrupted.

The hydrogenation catalyst used is a palladium/ligand complex.

Preferred ligands are the following: triphenylphosphine, diphenylphosphinoferrocene, tri-o-tolylphosphine, 1,2-bis (diphenylphosphino)ethane, 2,4-bis(diphenylphosphino) pentane, bis(diphenylphosphino)methane and tris(tertbutyl) phosphine. It is likewise possible to use mixtures of the ligands.

Palladium is generally employed as a palladium compound, from which the corresponding catalyst is prepared by addition of ligands. It is likewise possible to employ palladium as a complex having the correct stoichiometric composition to which, in accordance with the invention, an amount of ligand is added so that the ligand excess defined in accordance with the invention is observed.

Suitable palladium compounds employed in the presence of the excess of ligand are preferably the following: Tetrakis (triphenylphosphine)palladium(0), dibenzylidenepalladium (0) complexes, palladium on carbon (preferably 5%), $PdCl_2dppf$, palladium acetate/tri-O-tolylphosphine complex, Pd(0)*dppe, Pd(0)*dppp, Pd(0)*dppm, Pd(COD) $Cl_2$, $PdCl_2$, $Pd(OAc)_2$ and $PdBr_2$.

The molar ratio between palladium and the acid to be hydrogenated is preferably from 1:500 to 1:200, in particular from 1:50 to 1:100.

The molar ratio between palladium and ligand is from 1:5 to 1:15, preferably from 1:5 to 1:10, in particular from 1:5 to 1:6, in the case of monodentate ligands and from 1:2.5 to 1:7.5, preferably from 1:2.5 to 1:5, in particular from 1:2.5 to 1:3, in the case of bidentate ligands.

Non-solvent anhydrides used for the process are preferably pivalic anhydride, acetic anhydride, isobutyric anhydride, 5-norbornene-2,3-dicarboxylic anhydride, 1,2,3,6-tetrahydrophthalic anhydride and naphthalene-1,8-dicarboxylic anhydride.

The molar ratio between the carboxylic anhydride and the 5-arylnicotinic acid is preferably from 10:1 to 8:1, preferably from 7:1 to 6:1 and in particular from 5:1 to 2:1.

The compounds of the formula I can be obtained, after removal of the solvent, by conventional work-up steps, such as, for example, addition of water to the reaction mixture and extraction. It may be advantageous, for further purification of the product, subsequently to carry out a distillation or crystallization.

The compounds of the formula I which can be prepared by the process according to the invention are important intermediates or end products in industrial organic chemistry. Appropriately substituted derivatives are, in particular, valuable intermediates in the synthesis of highly value-added end products or are such end products themselves, for crop protection, such as, for example, fungicides, insecticides, herbicides or pesticides, or for the preparation of substances having high pharmaceutical activity.

Even without further embodiments, it is assumed that a person skilled in the art can utilize the above description in the broadest scope. The preferred embodiments should therefore merely be regarded as a descriptive disclosure which is not limiting in any way.

The examples below are intended to illustrate the invention without representing a limitation. Unless otherwise stated, percentages are percent by weight. All temperatures are given in degrees Celsius.

EXAMPLE 1

13.2 g of 4-fluorobenzeneboronic acid and 10.8 g of sodium hydrogen-carbonate are initially introduced, and a mixture of 16.1 g of 5-bromo-3-hydroxymethylpyridine, 30 ml of water and 60 ml of toluene is added with stirring and under a protective gas. A further 14 ml of water, 28 ml of toluene and 0.5 g of tetrakis(triphenylphosphine)palladium (0) are subsequently added. The reaction mixture is heated to reflux and held at this temperature for 2 hours. After cooling, the mixture is subjected to conventional work-up, giving 5-(4-fluorophenyl)nicotinyl alcohol. The alcohol is subsequently oxidized by conventional methods to give 5-(4-fluorophenyl)nicotinic acid.

EXAMPLE 2

1.38 kg of 5-bromonicotinic acid, 1.10 kg of 4-fluorobenzeneboronic acid and 0.40 kg of Pd/activated carbon (5%) are introduced into 8.5 liters of water. The black suspension is rendered alkaline using 1.39 kg of 32% sodium hydroxide solution and warmed to 100° C. After 4 hours, the mixture is subjected to conventional work-up, giving 5-(4-fluorophenyl)nicotinic acid.

Melting range: 198.5° C. to 203° C.

EXAMPLE 3

15.3 g of methyl 5-(4-fluorophenyl)nicotinate (obtainable by Suzuki coupling of methyl 5-bromopyridine-3-carboxylate with 4-fluorobenzeneboronic acid analogously to Example 1 or 2) are saponified by conventional methods to give 5-(4-fluorophenyl)nicotinic acid.

EXAMPLE 4

5-Bromo-3-acetoxymethylpyridine is reacted with 4-fluorobenzeneboronic acid as described in Example 1. The 5-(4-fluorophenyl)pyridin-3-ylmethyl acetate obtained is saponified by conventional methods and subsequently oxidized to give 5-(4-fluorophenyl)nicotinic acid.

EXAMPLE 5

5-(4-Fluorophenyl)nicotinic acid is dissolved in tetrahydrofuran in an autoclave, three equivalents of the respective acid anhydride are added, and the mixture is rendered inert by repeatedly injecting a protective gas. A solution of Pd(OAc)$_2$ and PPh$_3$ in tetrahydrofuran is added in a counter-current of protective gas, and the reaction solution is subsequently hydrogenated at 80° C. under a hydrogen pressure of 8 bar with stirring. Conventional work-up gives the aldehyde in a yield of 98%.

What is claimed is:

1. A process for the preparation of a 5-aryinicotinaldehyde of formula I

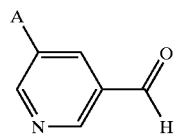

in which

A is a phenyl radical or naphthyl radical, each of which is unsubstituted, monosubstituted or polysubstituted by R, F, Cl, Br, I, —CN, —NO$_2$, —CF$_3$, —OCF$_3$, —OCHF$_2$, —OCF$_2$CF$_3$ or —OH and in which or more CH groups is optionally replaced by N, and R is H, a straight-chain or branched alkyl radical having 1 to 15 carbon atoms which is monosubstituted by —CF$_3$ or at least monosubstituted by fluorine, where, in addition, one more CH$_2$ groups is optionally independently replaced by —S—, —O—, —O—CO—, —CO—O— or —CH=CH— in such a way that heteroatoms are not directly adjacent, said process comprising reduction of a corresponding 5-aryinicotinic acid by catalytic hydrogenation in the presence of carboxylic anhydrides and a palladium/ligand complex, wherein molar ratio between palladium and ligand is from 1:5 to 1:15 in the case of monodentate ligands and from 1:2.5 to 1:7.5 in the case of bidentate ligands.

2. A compound of formula I

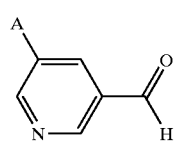

in which A is a 4-fluorophenyl group.

3. A process according to claim 1, further comprising reacting said 5-arylnicotinaldehyde with a primary amine to give a corresponding imine, and reducing to produce an N-alkylated amine.

4. A process according to claim 1, further comprising reacting a compound of formula I with a primary amine to give a corresponding imine, and reducing to produce an N-alkylated amine.

5. A process according to claim 3, wherein the N-alkylatedamine is one of formula X

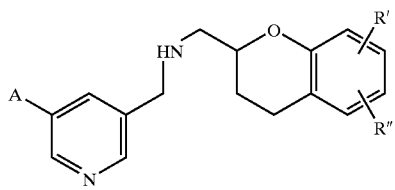

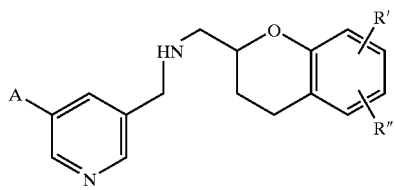

in which

R' and R", independently or one another, are H, straight-chain or branched alkyl radical having 1 to 15 carbon atoms which is monosubstituted by —CF$_3$ or at least monosubstituted by fluorine, where, in addition, one more CH$_2$ groups is optionally independently replaced by —S—, —O—, —O—CO—, —CO—O— or —CH═CH— in such a way that heteroatoms are not directly adjacent,or are F, Cl, Br, I, —CN, —NO$_2$, —CF$_3$, —OCF$_3$, —OCHF$_2$, —OCF$_2$CF$_3$, —OCHFCF$_3$ or —OH, and A is as defined above.

6. A process according to claim 4, wherein the N-alkylatedamine is one of formula X in which R' and R", independently or one another, are as defined for R or are F, Cl, Br, I, —CN, —NO$_2$, —CF$_3$, —OCF$_3$, —OCHF$_2$, —OCF$_2$CF$_3$, —OCHFCF$_3$ or —OH, and A is as defined above.

7. A process according to claim 5, wherein the N-alkylated amine is (R)-2-[5-(4-fluorophenyl)-3-pyridylmethylaminomethyl]chroman.

8. A process according to claim 6, wherein the N-alkylated amine is (R)-2-[5-(4-fluorophenyl)-3-pyridylmethylaminomethyl]chroman.

* * * * *

UNITED STATES PATENT AND TRADEMARK OFFICE
CERTIFICATE OF CORRECTION

PATENT NO. : 6,703,509 B2
DATED : March 9, 2004
INVENTOR(S) : Andreas Bathe et al.

It is certified that error appears in the above-identified patent and that said Letters Patent is hereby corrected as shown below:

Column 8,
Line 17, reads "5-aryinicotinaldehyde" should read -- 5-arylnicotinaldehyde --
Line 42, reads "5-aryinicotinic" should read -- 5-arylnicotinic --
Line 67, reads "N-alkylatedamine" should read -- N-alkylated amine --

Column 9,
Line 12, reads "independently or" should read -- independently of --
Line 19, reads "adjacent,or" should read -- adjacent, or --
Line 23, reads "N-alkylatedamine" should read -- N-alkylated amine --

Column 10,
Line 12, reads "independently or" should read -- independently of --

Signed and Sealed this

Twenty-first Day of December, 2004

JON W. DUDAS
*Director of the United States Patent and Trademark Office*